(12) United States Patent
Boelens et al.

(10) Patent No.: US 6,844,454 B2
(45) Date of Patent: Jan. 18, 2005

(54) PROCESS

(75) Inventors: Minne Boelens, Amsterdam (NL); Timothy Nisbet Nisbet, Amsterdam (NL)

(73) Assignee: Shell Oil Company, Houston, TX (US)

( * ) Notice: Subject to any disclaimer, the term of this patent is extended or adjusted under 35 U.S.C. 154(b) by 110 days.

(21) Appl. No.: 10/409,489

(22) Filed: Apr. 8, 2003

(65) Prior Publication Data

US 2003/0229236 A1 Dec. 11, 2003

(30) Foreign Application Priority Data

Apr. 12, 2002 (EP) .............................................. 02252618

(51) Int. Cl.⁷ .......................................... C07D 301/19
(52) U.S. Cl. ..................................................... 549/529
(58) Field of Search ......................................... 549/529

(56) References Cited

U.S. PATENT DOCUMENTS 3,351,635 A    11/1967  Kollar .................... 260/348.5
3,452,055 A     6/1969  Golden et al. ........... 260/348.5

FOREIGN PATENT DOCUMENTS

| EP | 0345856 | 5/1989 | ............ B01J/21/06 |
| EP | 0551929 | 1/1990 | ......... C01B/15/026 |
| GB | 1127987 | 9/1968 | ............ C07D/1/06 |
| WO | WO 99/42425 | 8/1999 | ............ C07C/15/44 |
| WO | WO 99/42426 | 8/1999 | ............ C07C/15/44 |
| WO | WO 99/58480 | 11/1999 | ............ C07C/15/46 |
| WO | WO 02/48126 | 6/2002 | ......... C07D/301/00 |

*Primary Examiner*—Taofiq Solola

(57) ABSTRACT

The invention relates to a process for the preparation of propylene oxide and an alkenyl aryl, which process involves:

(1) reacting an alkyl aryl hydroperoxide with propene to yield propylene oxide and an aryl alcohol; and, (2) contacting, at elevated temperature, feed containing the aryl alcohol obtained in step (1) with a heterogeneous dehydration catalyst to yield an alkenyl aryl, in which process the feed of step (2) has at most 0.30% wt of compounds having a molecular weight of at least 195.

5 Claims, No Drawings

PROCESS

FIELD OF THE INVENTION

The present invention relates to a process in which feed comprising aryl alcohol is contacted with catalyst, more specifically feed comprising 1-phenyl ethanol (also known as α-phenyl ethanol or methyl phenyl carbinol) and/or substituted 1-phenyl ethanol.

BACKGROUND OF THE INVENTION

A commonly known process in which aryl alcohol is converted with the help of a catalyst is a process in which propylene oxide and styrene are produced starting from ethylbenzene. In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl ethanol, and (iii) converting the 1-phenyl ethanol into styrene by dehydration using a suitable dehydration catalyst.

A further well-known process comprises the manufacture of propylene oxide with the help of cumene. In this process, cumene is reacted with oxygen or air to form cumene hydroperoxide. Cumene hydroperoxide thus obtained is reacted with propene in the presence of an epoxidation catalyst to yield propylene oxide and 2-phenyl propanol. The latter can be converted into cumene with the help of a heterogeneous catalyst and hydrogen. Suitable processes are described for example in WO 02/48126.

It was found that in the preparation of aryl alcohol, by-products are formed. Such by-products can be dimers and trimers of the aryl alcohol such as bis(aryl alkyl)ethers. In the process in which ethylbenzene is used, a major part of the bis(aryl alkyl)ethers formed was found to consist of bis(α,α-phenyl ethyl)ether, which is assumed to result from the reaction between two molecules of 1-phenyl ethanol. These by-products such as dimers and trimers are difficult to separate from the aryl-alcohol while they can also be formed during separation. In the past, not a lot of attention was paid to the presence of these by-products in the aryl alcohol.

In the conventional process described in U.S. Pat. No. 3,351,635, the distillation of the aryl alcohol containing reaction mixture is described in general terms. In the examples, the bottom fraction of the distillation is dehydrated. The bottom fraction will contain substantial amounts of heavy by-products. In the process of GB-A-1,127,987, a substantial amount of relatively heavy compounds is formed at the conditions at which the distillation columns are operated. A substantial amount of these relatively heavy compounds is distilled overhead and is processed further together with the alpha phenyl ethanol or dimethyl benzyl alcohol. The process of U.S. Pat. No. 3,452,055 makes use of a vaporizer for separating the different compounds. Vaporizers tend not to separate aryl alcohol from the dimer and trimer by-products.

SUMMARY OF THE INVENTION

It has now been found that the presence of small amounts of relatively heavy compounds such as the dimer and trimer by-products, can lead to deterioration of the product obtained in a subsequent process step. Products were observed to contain substantially more heavy compounds if the feed contained small amounts of relatively heavy compounds.

Therefore, the present invention now relates to a process for the preparation of propylene oxide, which process comprises:
(1) reacting alkyl aryl hydroperoxide with propene to yield propylene oxide and aryl alcohol, and
(2) contacting at elevated temperature feed comprising aryl alcohol obtained in step (1) with a heterogeneous catalyst, in which process the feed of step (2) comprises at most 0.30% wt of compounds having a molecular weight of at least 195.

DETAILED DESCRIPTION OF THE INVENTION

Within the further context of the present invention the expression aryl alcohol embraces compounds containing both an aromatic group and a hydroxyl group. The aryl alcohols preferably are phenyl substituted alcohols. More specifically, the aryl alcohol is an alkanol containing of from 2 to 6 carbon atoms and containing a phenyl substituent. More specifically, the aryl alcohol is 1-phenyl ethanol and/or substituted 1-phenyl ethanol. The substituents of 1-phenylethanol can be either on the phenyl ring or on the ethanol chain. A preferred substituted 1-phenyl ethanol is 2-phenyl propanol.

The feed comprising aryl alcohol for use in the present process is obtained from a preceding epoxidation step wherein alkyl aryl hydroperoxide is reacted with propene to yield propylene oxide and aryl alcohol. As mentioned above, alkyl aryl hydroperoxides which are conventionally used are cumene hydroperoxide and ethylbenzene hydroperoxide. Alkyl aryl hydroperoxide is reacted with propene to yield propylene oxide and aryl alcohol. In such epoxidation step a homogeneous catalyst or a heterogeneous catalyst can be applied. As homogeneous catalysts molybdenum compounds are frequently applied, while catalysts based on titanium on a silica carrier are often used as heterogeneous catalysts. Conditions under which epoxidation is carried out are known in the art and include temperatures of 75 to 150° C. and pressures up to 80 bar. The reaction medium is preferably in the liquid phase. The effluent from the epoxidation step is normally first subjected to a separation treatment to remove the propylene oxide formed, after which the residual stream, containing aryl alcohol, is suitably subjected to one or more further separation treatments. In such optional separation treatments, alkyl aryl can be removed for reuse in an earlier stage of the process.

In the process according to the invention, compounds having a molecular weight of at least 195 are separated from the aryl alcohol containing stream. The compounds which are separated off will generally have a molecular weight of more than 195. More preferably, the feed of the present invention comprises at most 0.30% wt of compounds having a molecular weight of at least 200. Examples of such compounds are diners and trimers of the alkyl aryl starting compounds, and diners and trimers of aryl alcohols. The amounts of these dimers and trimers preferably is below the amounts indicated hereinbelow. If the aryl alcohol is 1-phenyl ethanol, the amount of bis(α,α-phenyl ethyl)ether preferably is below the amounts indicated. If the aryl alcohol is 2-phenyl propanol, the amount of bis(2,2-phenyl propyl) ether is preferably below the amounts indicated.

Removal of the heavy compounds can be done in any way known to be suitable to someone skilled in the art. Suitable methods comprise flashing and distillation. However, care should be taken that these heavy compounds are removed to the low levels required according to the present invention. A conventional distillation will generally not give the low levels of heavy compounds which are required. The compounds should be removed such that the feed comprising aryl alcohol contains at most 0.30% wt of these heavy compounds, more preferably less than 0.30 % wt of these heavy compounds, more preferably at most 0.25% wt of these heavy compounds, more preferably at most 0.20% wt of these heavy compounds, more preferably less than 0.20% wt of these heavy compounds, more preferably at most 0.15% wt, more preferably less than 0.15% wt, more preferably at most 0.10% wt, more preferably less than 0.10% wt, more preferably at most 0.08% wt, most preferably less than 0.08% wt.

The amount of heavy compounds left in the feed will generally be at least 0.001% wt, more specifically at least 0.005% wt, most specifically at least 0.01% wt.

A preferred method of removing the heavy compounds as required according to the present invention, comprises distillation. Feed comprising aryl alcohol is preferably subjected to distillation in which distillation the aryl alcohol is distilled off and heavy compounds are removed as bottom product. The bottom product which is obtained in this way, can suitably be converted further for example by cracking. Such treatment has been described in EP-A-1056697. Distillate comprising aryl alcohol is a preferred feed for use in the present invention.

A preferred process for converting the feed comprising aryl alcohol comprises dehydration. This process is well known in the art. It can be carried out both in the gas phase and in the liquid phase. Suitable dehydration catalysts include for instance acidic materials like alumina, alkali alumina, aluminium silicates and H-type synthetic zeolites. Dehydration conditions are also well known and usually include reaction temperatures of 150–250° C. for liquid phase dehydration and 210–320° C., typically 280–310° C., for gas phase dehydration. Pressures usually range from 0.1 to 10 bar. In principle any known dehydration process can be applied in the process according to the present invention. For the purpose of the present invention gas phase dehydration is preferred. In a preferred embodiment the gas phase dehydration is carried out at a temperature in the range of 250 to 320° C. using an alumina-based dehydration catalyst.

Processes which are especially suitable for converting aryl alcohol into alkenyl aryl have been described in WO 99/58480. Such processes for the preparation of styrene comprise the gas phase dehydration of 1-phenyl-ethanol at elevated temperature in the presence of a dehydration catalyst, wherein the dehydration catalyst consists of shaped alumina catalyst particles having a surface area (BET) in the range of from 80 to 140 m$^2$/g and a pore volume (Hg) in the range of from 0.35 to 0.65 ml/g, of which 0.03 to 0.15 ml/g is in pores having a diameter of at least 1000 nm.

A further process which can be used has been described in WO 99/42425. These processes for the preparation of styrene or substituted styrenes comprise the gas phase dehydration of 1-phenyl ethanol or substituted 1-phenyl ethanol in the presence of a solid,acidic catalyst comprising a zeolite and a binder material, wherein the weight ratio of zeolite to binder is in the range of from 1:99 to 90:10 and wherein the following relation applies:

$$0<K<5 \tag{1}$$

with:

$$K=V/S*[(Pz*fz)+(Pb*fb)]^{1/2} \tag{2}$$

wherein:

V/S is the volume/surface ratio of the catalyst used in mm;

fz is the weight fraction of zeolite present in the catalyst in grams zeolite per gram catalyst;

fb is the weight fraction of binder present in the catalyst in grams binder per gram catalyst;

Pz is the intrinsic productivity of the zeolite expressed as grams styrene produced per gram of zeolite per hour, as measured for pure zeolite samples of small particle size (i.e. <0.1 mm) at the temperature applied in gas phase dehydration and at a conversion of 1-phenyl ethanol into styrene below 80%; and Pb is the intrinsic productivity of the binder expressed as grams styrene produced per gram of binder per hour, as measured for pure binder samples of small particle size (i.e. <0.1 mm) under the same conditions as used for determining Pz.

The product of the process of the present invention will generally either be an alkenyl aryl or an alkyl aryl. The product obtained will generally be subjected to a separation treatment before being reacted further. Preferably, the process according to the present invention is a dehydration process. The product of such process will comprise an alkenyl aryl, more specifically styrene. Such product will generally be separated into an alkenyl aryl rich fraction which also contains the dehydration water, and a residual fraction. Such separation can be effected in several ways, but most suitably is achieved by flashing or distillation. In such separation, the alkenyl aryl rich fraction will be removed as the top fraction, whilst a residual fraction containing heavy ends formed during the dehydration will be obtained as the bottom fraction.

Although the process according to the present invention gives a product which contains a relatively small amount of heavy compounds, it can be advantageous to treat the product of the present invention in a process as described in EP-A-1056697. The process of EP-A-1056697 comprises the steps of:

(a) subjecting-a feed containing 1-phenyl ethanol or substituted 1-phenyl ethanol to a dehydration treatment in the presence of a suitable dehydration catalyst, (b) subjecting the resulting product stream to a separation treatment, thus obtaining a stream containing styrene or substituted styrene and a residual fraction containing heavy ends, and (c) converting at least part of these heavy ends to styrene or substituted styrenes by subjecting a stream containing these heavy ends to a cracking treatment in the presence of an acidic cracking catalyst.

The invention is further illustrated by the following examples without restricting its scope to these particular embodiments.

EXAMPLE 1

In a reactor, air was blown through ethylbenzene. The product contained ethylbenzene hydroperoxide. This product was mixed with a solution containing NaOH. The neutralized mixture was subsequently water washed. The product obtained was reacted with propene in the presence of a titania on silica catalyst as described in the Example according to the teaching of EP-A-345856. Unreacted ethylbenzene was removed by distillation. Subsequently, the product was distilled. Different distillates were obtained, dependent on the way in which the distillation was carried out. In Table 1, the distillates are described.

TABLE 1

|  | 1 | comparative | 2 |
|---|---|---|---|
| 1-phenyl ethanol | 79.00 | 77.30 | 76.93 |
| 2-phenyl ethanol | 3.46 | 3.34 | 2.31 |
| acetophenone | 11.86 | 12.17 | 13.68 |
| further compounds $M_w < 195$ | 5.64 | 6.83 | 7.03 |
| compounds $M_w \geq 195$ | 0.04 | 0.36 | 0.05 |

The feeds described in Table 1 were subjected to a process as described in Example 1 of WO 99/58480. In this process 1-phenyl-ethanol was dehydrated to obtain styrene. The conversion obtained with the different feeds, is shown in Table 2. The amounts are % conversion of 1-phenyl ethanol in the feed.

TABLE 2

| Time (hours) | feed 1 | comparative feed | feed 2 |
|---|---|---|---|
| 8.5 | 99.51 | 99.23 | 99.52 |
| 21.5 | 99.75 | 99.20 | 99.52 |
| 34.5 | 99.73 | 99.16 | 99.41 |
| 47.5 | 99.63 |  | 99.24 |

The amount of heavy products (compounds having a $M_W \geq 195$) present in the products of these feeds, are shown in Table 3. The amounts given are % wt on styrene produced.

TABLE 3

| Time (hours) | feed 1 | comparative feed | feed 2 |
|---|---|---|---|
| 8.5 | 3.06 | 4.10 | 3.59 |
| 21.5 | 3.37 | 4.48 | 3.50 |
| 34.5 | 3.28 | 5.06 | 3.44 |
| 47.5 | 3.23 |  | 3.30 |

We claim:

1. A process for the preparation of propylene oxide and an alkenyl aryl, which process comprises:

(1) reacting an alkyl aryl hydroperoxide with propene to yield propylene oxide and an aryl alcohol; and, (2) contacting, at elevated temperature, feed comprising the aryl alcohol obtained in step (1) with a heterogeneous dehydration catalyst to yield an alkenyl aryl, in which process the feed of step (2) comprises at most 0.30% wt of compounds having a molecular weight of at least 195.

2. The process according to claim 1, in which process the aryl alcohol is selected from the group consisting of 1-phenyl ethanol and substituted 1-phenyl ethanol.

3. The process according to claim 2, in which the feed is a distillate comprising aryl alcohol.

4. The process according to claim 3, wherein the feed comprises at least 0.001% wt of compounds having a molecular weight of at least 195.

5. The process according to claim 1, in which process the catalyst comprises an alumina-based catalyst.

* * * * *